United States Patent
Zingerman

(10) Patent No.: US 9,192,346 B2
(45) Date of Patent: Nov. 24, 2015

(54) SYSTEMS AND METHODS FOR MULTI-MODALITY IMAGING

(71) Applicant: General Electric Company, Schenectady, NY (US)

(72) Inventor: Yulim Zingerman, Tirat Carmel (IL)

(73) Assignee: General Electric Company, Schenectady, NY (US)

( * ) Notice: Subject to any disclaimer, the term of this patent is extended or adjusted under 35 U.S.C. 154(b) by 120 days.

(21) Appl. No.: 14/134,205

(22) Filed: Dec. 19, 2013

(65) Prior Publication Data
US 2015/0173696 A1    Jun. 25, 2015

(51) Int. Cl.
| | |
|---|---|
| *G01N 23/04* | (2006.01) |
| *A61B 6/00* | (2006.01) |
| *A61B 6/03* | (2006.01) |
| *A61B 6/04* | (2006.01) |

(52) U.S. Cl.
CPC ............... *A61B 6/4447* (2013.01); *A61B 6/032* (2013.01); *A61B 6/035* (2013.01); *A61B 6/037* (2013.01); *A61B 6/0407* (2013.01); *A61B 6/0457* (2013.01); *A61B 6/4014* (2013.01); *A61B 6/4417* (2013.01)

(58) Field of Classification Search
CPC ...... A61B 6/032; A61B 6/4417; A61B 6/037; A61B 8/483; A61B 6/5247; A61B 6/035; A61B 6/04; A61B 6/5235
USPC .......................................................... 378/63
See application file for complete search history.

(56) References Cited

U.S. PATENT DOCUMENTS

| | | | | |
|---|---|---|---|---|
| 5,391,877 | A | * | 2/1995 | Marks ....................... 250/363.04 |
| 2004/0262525 | A1 | * | 12/2004 | Yunker et al. ............. 250/363.08 |
| 2010/0290584 | A1 |   | 11/2010 | Vesel et al. |
| 2011/0129061 | A1 | * | 6/2011 | Janbakhsh ...................... 378/19 |

FOREIGN PATENT DOCUMENTS

WO        2013168111 A2    11/2013

OTHER PUBLICATIONS

Search Report and Written Opinion from Corresponding PCT Application No. PCT/US2014/050726, dated Oct. 23, 2014; 12 pages.

* cited by examiner

*Primary Examiner* — Courtney Thomas
(74) *Attorney, Agent, or Firm* — Dean D. Small; The Small Patent Law Group, LLC

(57) ABSTRACT

A medical imaging system is provided that includes a first gantry having a plurality of first detector units coupled within a bore of the first gantry such that the first detector units form a first field of view (FOV) of the first gantry. The first detector units are configured to acquire SPECT data. Further, the medical imaging system includes a second gantry having a plurality of second detector units coupled within a bore of the second gantry such that the second detector units form a second FOV of the second gantry. The second detector units are configured to acquire x-ray CT data. The second gantry is positioned adjacent to the first gantry. The medical imaging system also includes a patient table movable through the bores and a controller unit configured to control a rotation speed of the first detector units and the second detector units around the examination axis.

14 Claims, 10 Drawing Sheets

SYSTEMS AND METHODS FOR MULTI-MODALITY IMAGING

BACKGROUND OF THE INVENTION

Embodiments described herein generally relate to imaging systems, particularly to multi-modality imaging systems, such as Single Photon Emission Computed Tomography (SPECT) and Computed Tomography (CT) imaging systems.

CT imaging systems typically include an x-ray source and a detector. In operation, the x-ray source and the detector are rotated around an object to be imaged such that an angle at which an x-ray beam intersects the object changes. A group of x-ray attenuation measurements, or projection data, from a detector at one gantry angle may be referred to as a "view." A set of views made at different gantry angles during one revolution of the x-ray source and detector may be referred to as a "scan." In an axial scan, projection data is processed to construct an image that corresponds to a two-dimensional cross-section or slice of an object being scanned.

SPECT imaging systems, such as Nuclear Medicine (NM) imaging systems, use radioactive isotopes injected into the patient and multiple detectors or detector heads to measure emitted photons to acquire image information using a plurality of detectors. Additionally, in NM imaging systems, the resolution of the detector, such as a gamma detector, is determined by the resolution of the detector (based on the size of pixels of the detector) and the resolution of a collimator attached to the detector. The resolution degrades with distance of the detector, specifically the collimator, from the subject. Thus, the detectors are positioned adjacent to the subject to increase resolution of the NM data.

It can be beneficial to utilize both CT and NM systems to scan a subject such as in known dual-modality imaging systems. In these dual-modality imaging systems separate gantries are typically used. However, having two imaging detector gantries (in tandem) increases the footprint of the system and consequently a larger imaging room or space is needed. Moreover, dual-modality imaging systems that combine the imaging components into a single gantry add complexity to the design and control of the system.

Further, newer CT detectors have an increasingly higher field of view, which increase the CT detector size. The larger CT detector in these dual-modality CT/NM systems results in the NM detector being displaced farther along the examination axis. Thus, the patient travels farther into the bore volume, which can cause claustrophobia and general discomfort for certain patients. In addition, as a result of the increased travel length, the patient table has to be made stronger with additional reinforcements to prevent sagging of the bed as the patient travels through the bore. Further, the increased travel length increases the likelihood the patient may move during the scan creating issues or complexities during registration or alignment between the CT and NM images.

BRIEF DESCRIPTION OF THE INVENTION

In an embodiment, a medical imaging system is provided that includes a first gantry having a plurality of first detector units coupled within a bore of the first gantry such that the first detector units form a first FOV of the first gantry. The first detector units are configured to acquire Single Photon Emission Computed Tomography (SPECT) data. Further, the medical imaging system includes a second gantry having a plurality of second detector units coupled within a bore of the second gantry such that the second detector units form a second FOV of the second gantry. The second detector units are configured to acquire x-ray computed tomography (CT) data. Additionally, the second gantry is positioned adjacent to the first gantry. The medical imaging system also includes a patient table movable through the bores of the first and second gantry along an examination axis, as well as a controller unit configured to control a rotation speed of the first detector units and the second detector units around the examination axis.

In another embodiment, a method is provided for a dual-modality imaging system. The method includes adjoining a first gantry having a plurality of first detector units configured to acquire Single Photon Emission Computed Tomography (SPECT) data and a second gantry having a plurality of second detector units to acquire x-ray computed tomography (CT) data such that a common bore is formed through each gantry along an examination axis, wherein the first detector units are coupled within a portion of the common bore formed through the first gantry. The method further includes positioning an object on a patient table that is movable through the common bore along the examination axis. Positioning the first detector array in an imaging position when the object is positioned at a field of view (FOV) of the first detector units, and acquiring SPECT data of the object. The method also includes positioning the object into a FOV of the second detector array, and acquiring x-ray CT data of the object.

In another embodiment, a method for obtaining a multimodality image of a patient is provided. The method includes providing an NM-CT multimodality imaging system having a gap between the FOV of NM detectors and the FOV of CT detector of less than 50 cm. The method also includes acquiring a CT image and an NM image of a patient, wherein said acquiring of the CT image and the NM image of the patient is performed without repositioning said patient with respect to the patient table. Further, the CT image and the NM image overlap over at least 120 cm along the patient's length.

DETAILED DESCRIPTION OF THE INVENTION

Figure 1:
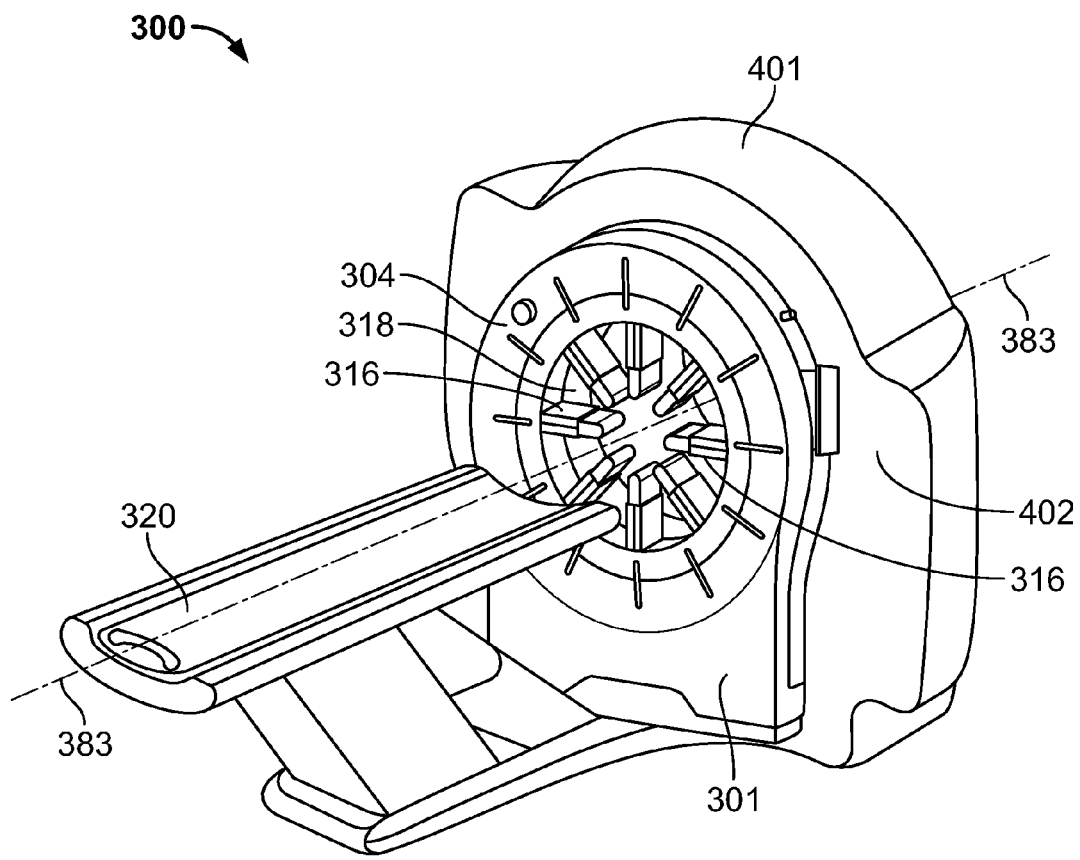
FIG. 1 is an illustration of a perspective view of a dual-modality imaging system in accordance with an embodiment.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry or software. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments described herein provide methods and systems for reducing spacing between or the field of view (FOV) gap between two imaging modalities. For example, in some embodiments a nuclear medicine (NM) imaging system is provided that is configured as a Single Photon Emission Computed Tomography (SPECT) system with an array of detector heads within the footprint of a bore gantry, wherein detector units of the detector heads are individually and independently movable. In some embodiments, one or more of the detector units are capable of a plurality of types of movement, such as rotation and linear motion. The detector heads with the detector units may be configured to be positioned adjacent or proximate to a subject with the detector units rotated or swung, such as to increase the field of view of the detector units. At least one technical effect of some embodiments described herein is reducing the size of the gantry and/or decreasing the FOV gap between the two modalities.

FIG. 1 is a diagram illustrating a dual-modality imaging system 300 in accordance with various embodiments. A Nuclear Medicine (NM) imaging system 301 configured as a SPECT imaging system is shown with a plurality of arms 316 mounted to a gantry 304. The NM imaging system 301 adjoins or is positioned adjacent with a computed tomography (CT) imaging system 401. The CT imaging system 401 includes a gantry 402 having at least one x-ray source 411 and at least one x-ray detector array 410 (shown in FIG. 2). Each gantry 304 and 402 in the illustrated embodiment is formed from a discrete housing of the NM imaging system 301 and the CT imaging system 401 respectively, thus, allowing each of the gantries 304 and 402 to rotate at different rotational speeds. For example, the gantry 402 of the CT imaging system 401 may rotate at a rotational speed of 1 revolution per second, compared to a system having a combined or integrated gantry supporting a NM and CT imaging components which may rotate at a rotational speed of 1 revolution per 12 seconds. However, it should be appreciated that in other embodiments the rotational speed of the gantries 304 and 402 may be more or less relative to the above example. The higher rotational speed of the gantry 402 enables the CT imaging system 401 to acquire a higher quality CT image relative to a CT image acquired at a slower rotational speed. It should be appreciated that in some embodiments, the NM imaging system 301 and CT imaging system 401 are separate units, but may be housed in a common housing or enclosure. Further it should be noted that the dimension, size, shape, and/or positioning of the NM imaging system 301 and the CT imaging system 301 relative to each other may vary in other embodiments than as illustrated in FIG. 1.

Additionally, the gantries 304 and 402 form a common bore 318 therethrough extending from the entrance of the NM imaging system 301 to the exit of the CT imaging system 401 in the illustrated embodiment. The NM imaging system 301 is shown positioned in front of the CT imaging system 401 such that a patient enters the NM imaging system 301 before the CT imaging system 401 while moving through the common bore 318 along an examination axis 383. Thus, the common bore 318 allows acquiring a CT image and an NM image of the patient without repositioning the patient with respect to the patient table. Alternatively, the CT imaging system 401 may be positioned in front of the NM imaging system 301 such that the patient enters the CT imaging system 401 before the NM imaging system 301 while moving through the common bore 318 along an examination axis 383. Alternatively, the NM imaging system 301 and the CT imaging system 401 may be integrated into a single gantry as described herein.

Figure 2:
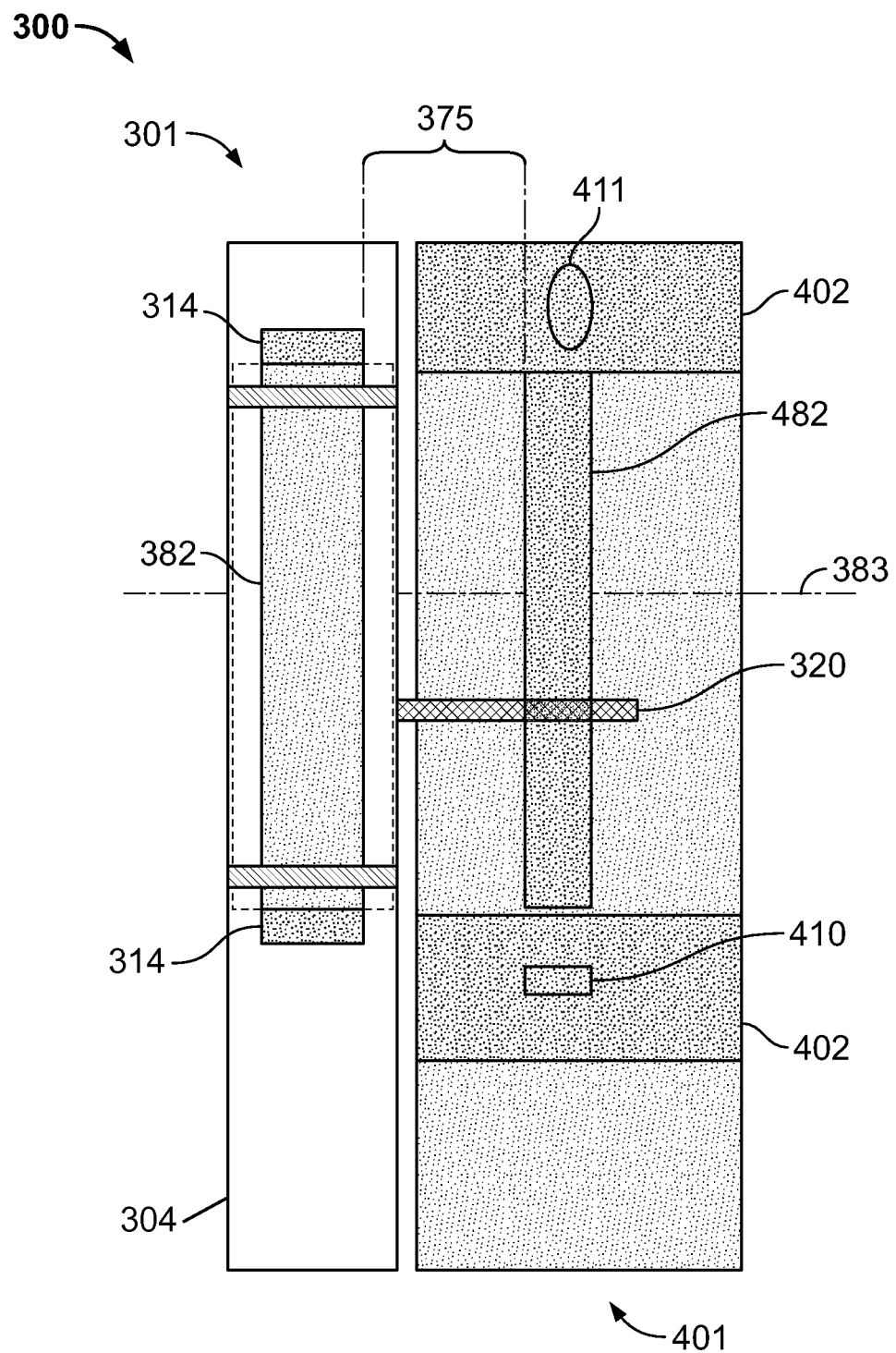
FIG. 2 is an illustration of a side view of a dual-modality imaging system in accordance with an embodiment.

FIG. 2 illustrates a side view of the dual-modality imaging system 300 in accordance with various embodiments. It should be noted that the width and depth of the gantries 304 and 402 illustrated in FIG. 2 may be different relative to each other or be approximately the same in other various embodiments. In the illustrated embodiment, the components of the imaging systems 301 and 401 are contained within the respective gantries 304 and 402, such that none of the NM imaging system 301 or CT imaging system 401 components are outside the gantry footprint. It should be noted that although the height of the gantries 304 and 402 are illustrated as being equal in FIG. 2, the gantry heights may vary with respect to each other in other various embodiments. However, regardless of differences in the respective heights of the gantries 304 and 402, the gantries 304 and 402 are positioned to have the common bore 318 along the examination axis 383.

Figure 4:
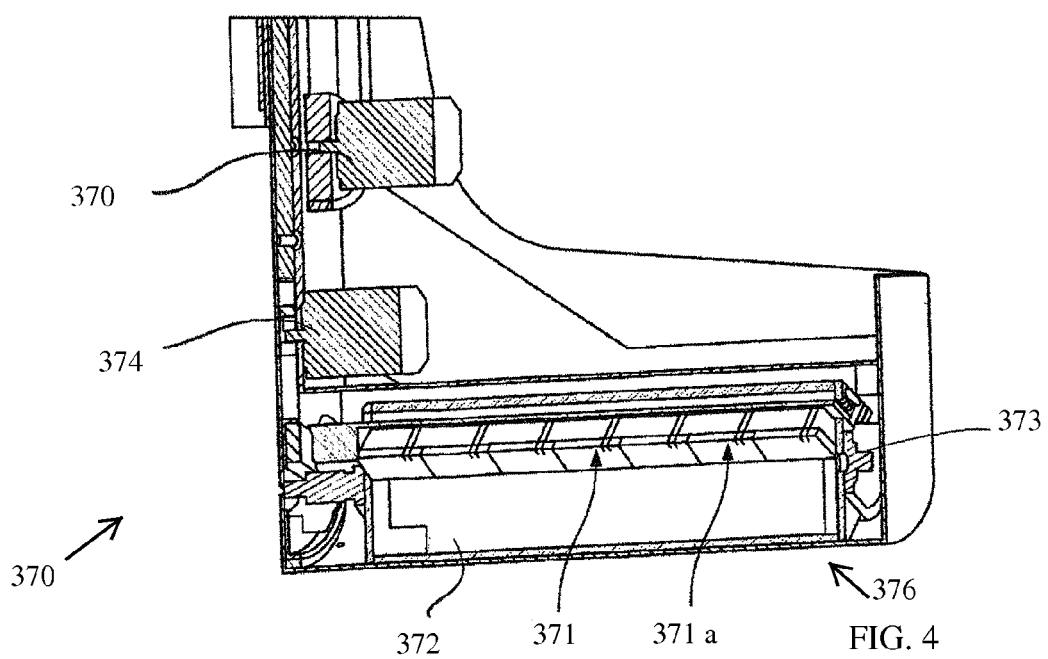
FIG. 4 is a diagram illustrating a detector arm configuration of a NM imaging system in accordance with an embodiment.

The arms 316 of the NM imaging system 301 may include a plurality of detector units 314 (shown, for example, in FIG. 7) forming a NM field of view (FOV) 382. Additionally or alternatively the arms 316 may include a plurality of imaging modules 371 (as illustrated in FIG. 4). In some embodiments, the detector units 314 are embodied as the imaging modules 371. The detector units 314 have a reduced size relative to whole body or general purpose image detectors, such as the NM cameras 608 (shown in FIGS. 11-12), and reduces the size of the gantry 304. The reduced gantry size reduces a FOV gap 375 shown between an edge of the NM FOV 382 that is nearest to the CT imaging system 401 and an edge of the CT FOV 482, which is formed from x-ray source 411 and x-ray detector array 410, that is nearest to the NM imaging system 301. The FOV gap 375 of an embodiment may be less than 50 cm long, for example, approximately 20 cm long, which may result in a reduction of 80 cm relative to the FOV gap 630 of a dual-modality imaging system 600 (shown in FIG. 12). In another embodiment the FOV gap 375 may be less than 40 cm long. Alternatively, the FOV gap 375 may be less than 30 cm long. The close proximity between the NM FOV 382 and CT FOV 482 allows for a reduction in the patient travel time between the NM image system 301 and the CT image system 401.

It should be noted that having the NM imaging system 301 and the CT imaging system 401 adjacent to each other allows a CT image and an NM image acquired from the dual-modality imaging system 300 to overlap in the same location or region of interest scanned of the patient. Further, having a reduced table travel length for the NM imaging system 301 and the CT imaging system 401 allows a longer coverage of the patient without the need to reposition the patient (e.g., head first and then feet first) to acquire images of the patient during a single scan. For example, as the patient travels through the common bore 318 the NM imaging system 301 and the CT imaging system 401 may continually acquire images of the patient such that an overlap of at least 120 cm of the patient acquired or scanned by both imaging system 301 and 401. However, it should be appreciated that the overlap may be more or less in other embodiments. Further, the close proximity between the NM FOV 382 and CT FOV 482 decreases the possibility of sag of the patient table 320 caused by the weight of the patient due to the decreased length of the bore 318 (and the examination axis 383). Additionally, the reduced gap allows for using thinner, less rigid patient pallet, thus reducing the gamma and x-ray absorption of the patient and increasing the NM resolution (which degrades with the distance to the patient). It should be further noted that a small gap is illustrated between the gantries 304 and 402 of the NM imaging system 301 and the CT imaging system 401. However, in other various embodiments no gap is present between the gantries 304 and 402 to further reduce the FOV gap 375.

Figure 3:
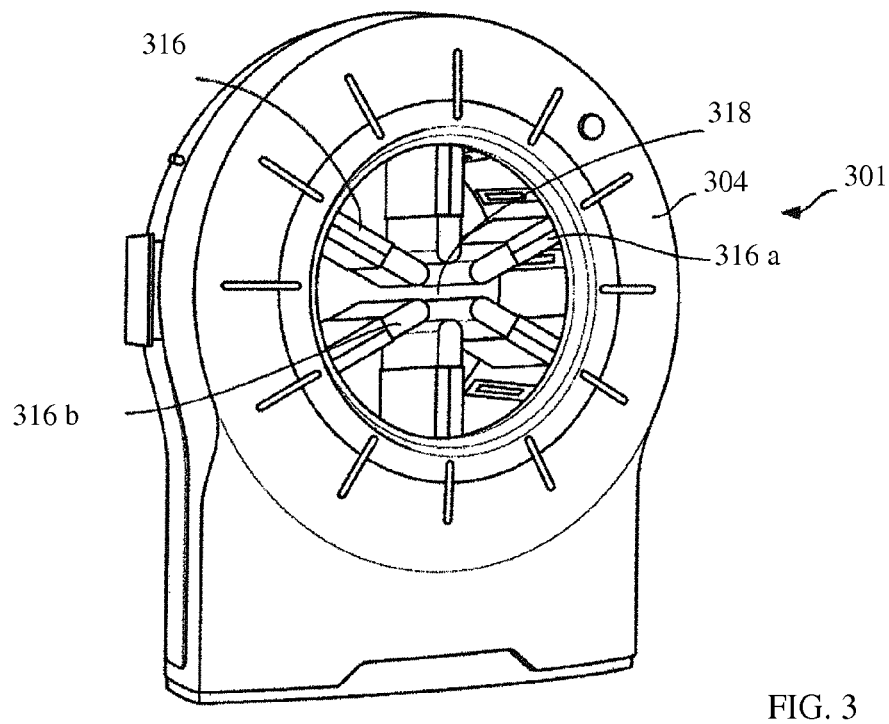
FIG. 3 is a perspective view of a Nuclear Medicine (NM) imaging system in accordance with an embodiment.

FIG. 3 is a perspective view of an embodiment of the NM imaging system 301 of the dual-modality imaging system 300. The system 300 may be provided with a gantry 304 having the plurality of arms 316 (e.g., movable supports as described herein) that extend and/or are movable radially inward and outward from the gantry 304. The arms 316 may be spaced apart circumferentially around the entire bore 318. It also should be noted that additional or fewer arms and different spacing between arms 316 may be provided, as well as not extending along the entire inner circumference of the bore 318. The arms 316 may be movable as described herein and may be embodied as the detector carriers 516 (shown in FIG. 9) in some embodiments. Additionally, each arm 316 may support one or more detector units or modules (e.g., detector modules 371 shown in FIG. 4, detector units 314 shown in FIG. 7, detector units 514 shown in FIG. 9). Other variations include arms 316 that are provided along only a portion of the circumference of the bore 318. Thus, it should be noted that although the arms 316 are shown positioned around the bore 318 or 360 degrees, the arms 316 may be provided along more or less of the bore 318, such as more or less than 360 degrees (e.g., 180 degrees). It also should be noted that for a configuration of less than 360 degrees, rotations may be used to provide imaging in both prone and supine positions of a subject (e.g., patient). For example, in some embodiments, having a configuration positioned along about 180 degrees, a rotation of about 210 degrees is provided to provide imaging in both the prone and supine position of the subject. However, the rotation may be more or less than 210 degrees as desired or needed.

The mechanism or components moving the imaging detectors in various embodiments may be provided using different arrangements. An arrangement 370 is shown in FIG. 4 illustrating an imaging detector configuration wherein a detector head 376 is mounted at one end of an arm (e.g., 316) that includes a rail to allow radial movement. The movement may be controlled, such as by a controller unit 330 (shown in FIG. 7), using a radial motion motor 370. The detector head 376 in this embodiment includes a plurality of imaging modules 371 (illustrated as CZT modules) that may be aligned in one or more rows (a single row is illustrated in the embodiment shown). As can be seen, a collimator 372 may be provided and coupled to one or more of the imaging modules 371. The collimator 372 may be provided as described herein. Additionally, the imaging modules 371 are coupled to a support 373 (e.g., a rod) that allows rotation or pivoting movement of the imaging modules 371 within the detector head 376. For example, a motor, such as a sweep motor 374 may be provided to control and move the imaging modules 371 along a sweep range transverse to the examination axis by having the imaging modules 371 rotate or pivot a defined number of degrees directed towards the region of interest. Optionally, the width of the NM FOV 382 may be changed by removing or adding imaging module 371 to the detector head 376.

Additionally, different configurations may be provided. For example, within a single cover or a single detector head, multiple detector units or modules may be provided. Additionally, one or more detectors may be fixed or mounted (or within) the patient table 320 or a support portion thereof.

Additionally or alternatively, the plurality of imaging modules 371 may represent multiple modalities such as NM imaging and CT imaging modalities allowing for a multi-modality imaging integrated into a single gantry. For example, arm 316a may include imaging module 371a which is configured as an x-ray source for the CT imaging modality and adjacent to a plurality of imaging modules 371 configured as CZT modules for the NM imaging modality. Opposite the arm 316a and the arm 316b may include an imaging module which is configured to detect x-rays. Thus, in some embodiments, a single gantry configuration may be provided that acquires NM imaging and CT imaging concurrently.

Figure 5:
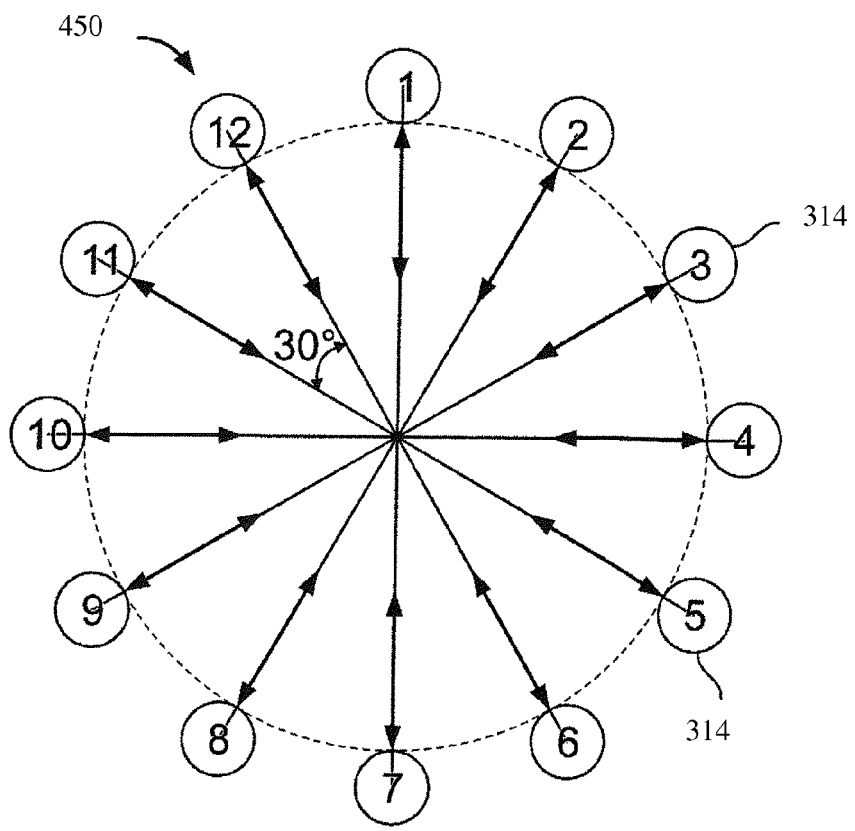
FIG. 5 is a diagram illustrating motion of detectors in accordance with an embodiment.
Figure 6:
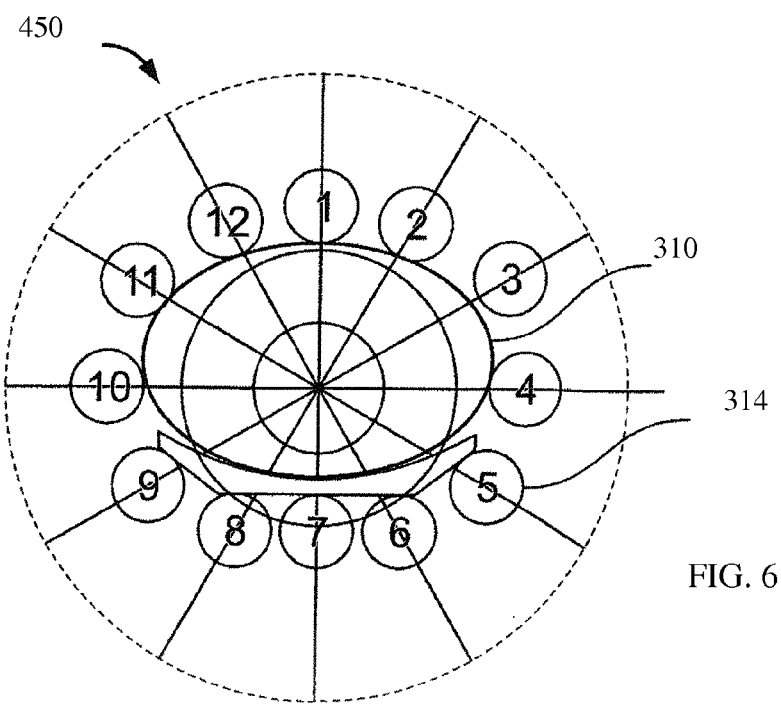
FIG. 6 is a diagram illustrating motion of detectors in accordance with an embodiment.
Figure 7:
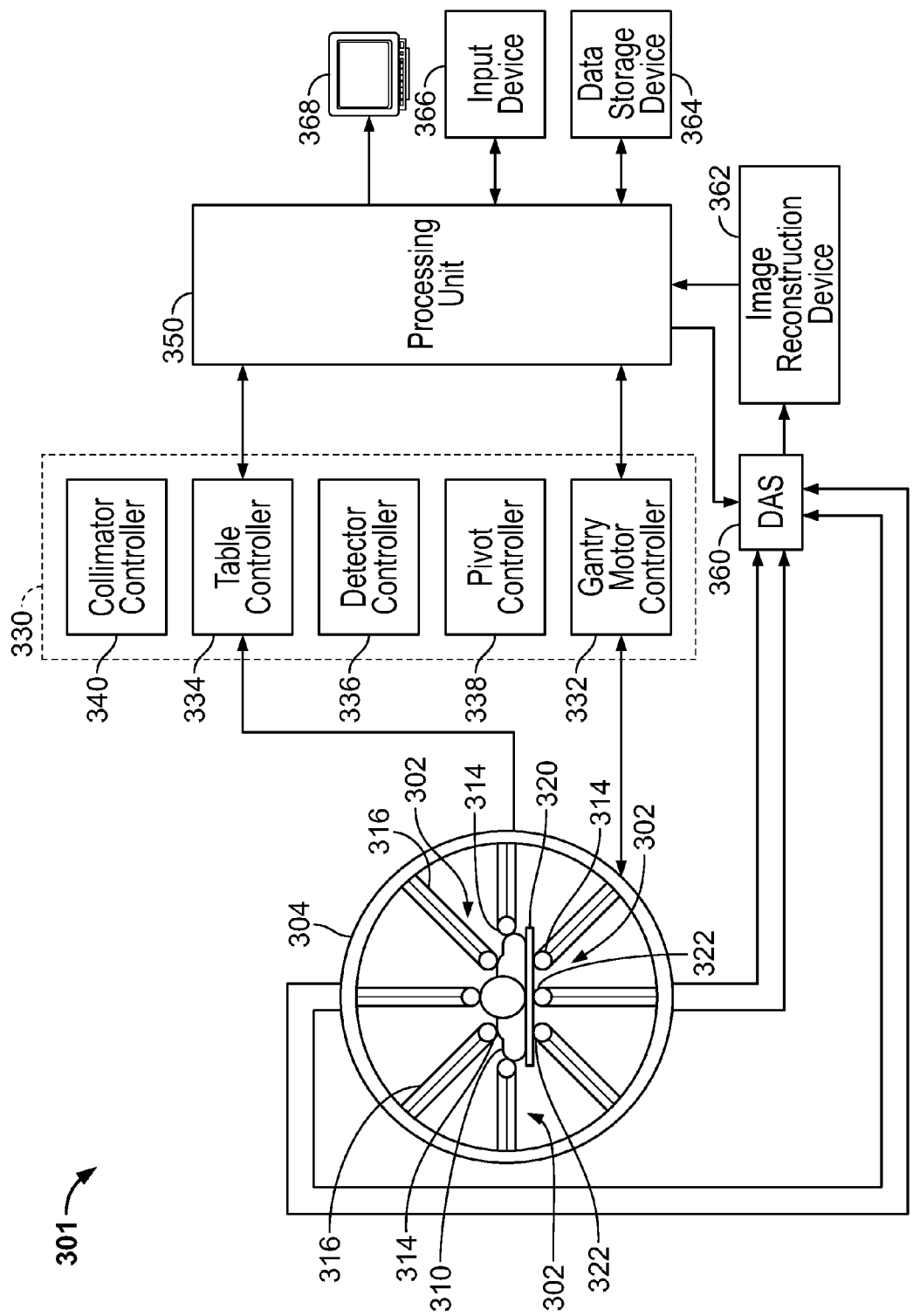
FIG. 7 is a schematic block diagram illustrating a NM imaging system in accordance with an embodiment.

In operation, and as shown, for example, in the imaging system 450 of FIGS. 5 and 6, the plurality of detector units 314, are positioned and spaced evenly along the circumference of a gantry forming an iris formation, such as shown in FIGS. 1, 3 and 7, and described and shown in a co-pending U.S. patent application Ser. No. 14/040,079, entitled "SYSTEMS AND METHODS FOR PLANAR IMAGING WITH DETECTORS HAVING MOVING DETECTOR HEADS," which is hereby incorporated by reference in its entirety. The detector units 314 are shown as spaced apart by 30 degrees, but other spacings may be provided. For example, an uneven spacing and/or additional or fewer detectors units 314 may be provided. As can be seen, the detector units 314 are movable radially inward and outward to position the detector units 314 adjacent to the subject 310 for imaging (shown in FIG. 6 in an imaging position or state). Thus, in this embodiment for example, the detector units 314 are shown in an outermost position in FIG. 5 and in an imaging position in FIG. 6. As should be appreciated, the detector units 314 are movable at different distances (e.g., one or more detector units 314 moved different distances) depending on the size, shape, etc., of the subject 310.

FIG. 7 is a schematic illustration of an embodiment of the NM imaging system 301 of the dual-modality imaging system 300. In the illustrated embodiment, imaging detectors 302 may include one or more detector units 314 that are coupled and supported by the plurality of arms 316 (e.g., a support arm or actuator that may be driven by a motor to cause movement thereof). The arms 316 are mounted within the bore 318 and extends from the gantry 304 surrounding a subject 310 (e.g., a patient). In some embodiments, the arm 316 allows radial movement of the detector units 314 towards and away from the subject 310. However, other configurations and orientations are possible as described herein beyond the radial or iris configuration shown in FIG. 7. It should be noted that the arm 316 may be any type of support that allows movement of the detector units 314 relative to the gantry 304, which in various embodiments, allows the detector units 314 to move radially or linearly towards and away from the gantry 304 and/or subject 310.

Figure 11:
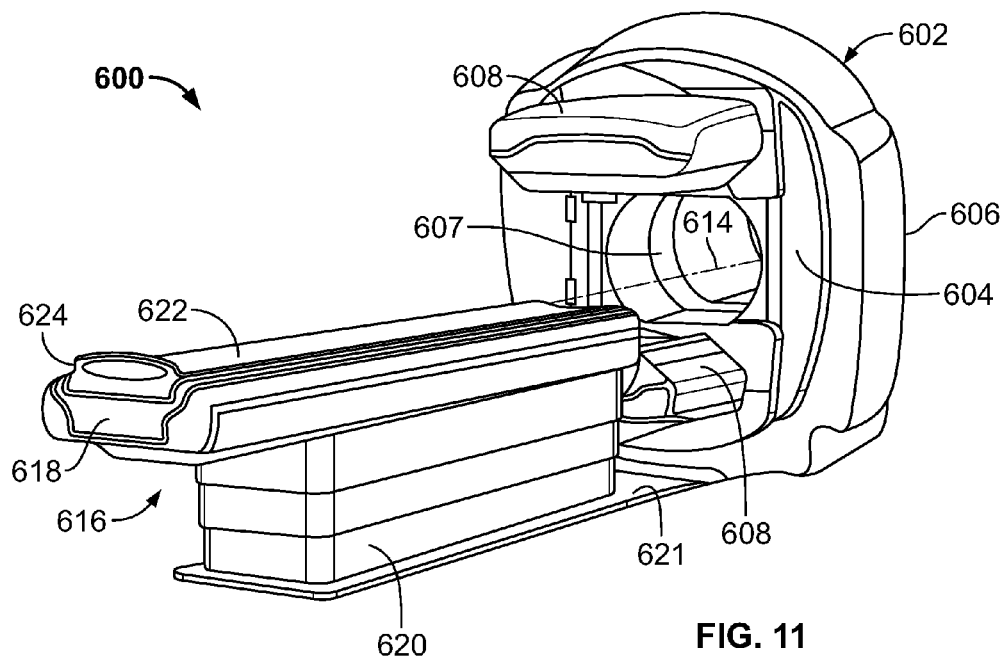
FIG. 11 is an illustration of a perspective view of a dual-modality system in accordance with another embodiment.

Each of the imaging detectors 302 in various embodiments are smaller than a whole body or general purpose imaging detector such as the NM cameras 608 of an embodiment in FIG. 11. The general purpose imaging detector 608 may be large enough to image most or all of a width of a patient's body at one time and may have a diameter or a larger dimension of approximately 50 cm or more. In contrast, the imaging detectors 302 may have dimensions of 4 cm to 20 cm and may be formed of Cadmium Zinc Telluride (CZT) tiles or modules. For example, each of the detector units 314 may be 8×8 cm in size and be composed of a plurality of CZT pixelated modules (not shown). For example, each module may be 4×4 cm in size and have 16×16=256 pixels. In some embodiments, each detector unit 314 includes a plurality of modules, such as an array of 1×7 modules. Optionally, different configurations and array sizes are contemplated including, for example, detector units 314 having multiple rows of modules.

It should be understood that the imaging detectors 302 may be different sizes and/or shapes with respect to each other, such as square, rectangular, circular or other shape. An actual FOV of each of the imaging detectors 302 may be directly proportional to the size and shape of the respective imaging detector.

The gantry 304 may be formed with the bore 318 (e.g., opening or aperture) therethrough as illustrated in FIG. 1. The patient table 320, such as a patient bed, is configured with a support mechanism (not shown) to support and carry the subject 310 in one or more of a plurality of viewing positions within the bore 318 and relative to the imaging detectors 302. Alternatively, the gantry 304 may comprise a plurality of gantry segments (not shown), each of which may independently move a support member or one or more of the imaging detectors 302.

The gantry 304 may also be configured in other shapes, such as a "C", "H" and "L", for example, and may be rotatable about the subject 310. For example, the gantry 304 may be formed as an open arc or arch which allows the subject 310 to be easily accessed while imaging and facilitates loading and unloading of the subject 310, as well as reducing claustrophobia in some subjects 310.

Additional imaging detectors (not shown) may be positioned to form rows of detector arrays or an arc around the subject 310. By positioning multiple imaging detectors 302 at multiple positions with respect to the subject 310, such as along the examination axis 383 (e.g., head to toe direction of the subject 310), image data specific for a larger FOV may be acquired more quickly.

Each of the imaging detectors 302 has a radiation detection face, which is directed towards the subject 310 or a region of interest within the subject 310. The radiation detection faces are each covered by or have coupled thereto a collimator 322. The actual FOV for each of the imaging detectors 302 may be increased, decreased, or relatively unchanged by the type of collimator 322. In some embodiments, the collimator 322 may include at least some collimator bores having different axial lengths. For example, collimator bores having varied lengths creating a curved face may be provided, such as described and shown in a co-pending U.S. patent application Ser. No. 14/040,608, entitled "SYSTEMS AND METHODS FOR CONTROLLING MOTION OF DETECTORS HAVING MOVING DETECTOR HEADS," which is hereby incorporated by reference in its entirety.

In one embodiment, the collimator 322 is a multi-bore collimator, such as a parallel hole collimator. However, other types of collimators, such as converging or diverging collimators may optionally or alternatively be used. Other examples for the collimator 322 include pinhole, parallel-beam converging, diverging fan-beam, converging or diverging cone-beam, multi-bore converging, multi-bore converging fan-beam, multi-bore converging cone-beam, multi-bore diverging, or other types of collimator. It should be noted that some multi-pinhole systems may acquire NM images while the NM detectors are stationary.

Optionally, multi-bore collimators may be constructed to be registered with pixels of the detector units 314, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

Figure 8:
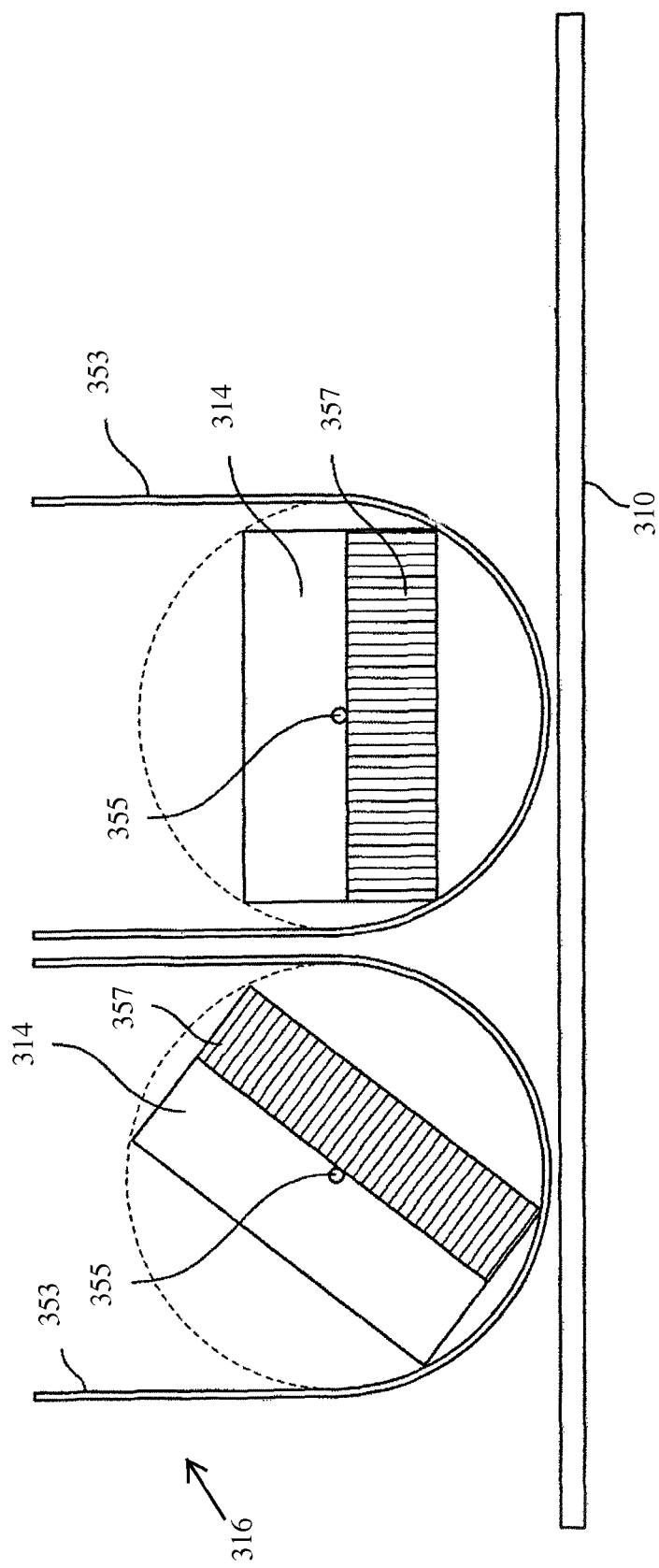
FIG. 8 is a schematic block diagram illustrating movement of detector units in accordance with an embodiment in one position.

FIG. 8 schematically demonstrates an embodiment of the detector unit 314 within a housing 353 of the arm 316 having only a single rotating or pivoting point. The arms 316 are shown in the imaging position being adjacent or approximate to the subject 310. The detector units 314 (e.g., a CZT detector), for example, may be equipped with a flat collimator 357 (e.g., collimator having a planar face). The detector unit 314 rotates about a fixed pivot point 355 along the sweep range transverse to the subject 310 and/or examination axis (e.g., the examination axis 383). Additionally, the rotation of the detector unit 314 enables the detector unit 314 to avoid collision with the subject 310 (illustrated as a substantially flat patient). Optionally, the sweep range of the detector unit 314 may be expanded during imaging, by having the arms 316 rotate around the bore 318.

In operation, a combined motion of the detector units 314 and the arm 316 is used to position the detector units 314 or move the detector units 314 before, during, and/or after imaging. The rotational (or pivoting) movement of the detector units 314 and up/down motion of the arm 316 are performed to reduce or minimize the distance from the face of the collimator 357 and the subject 310.

Figure 9:
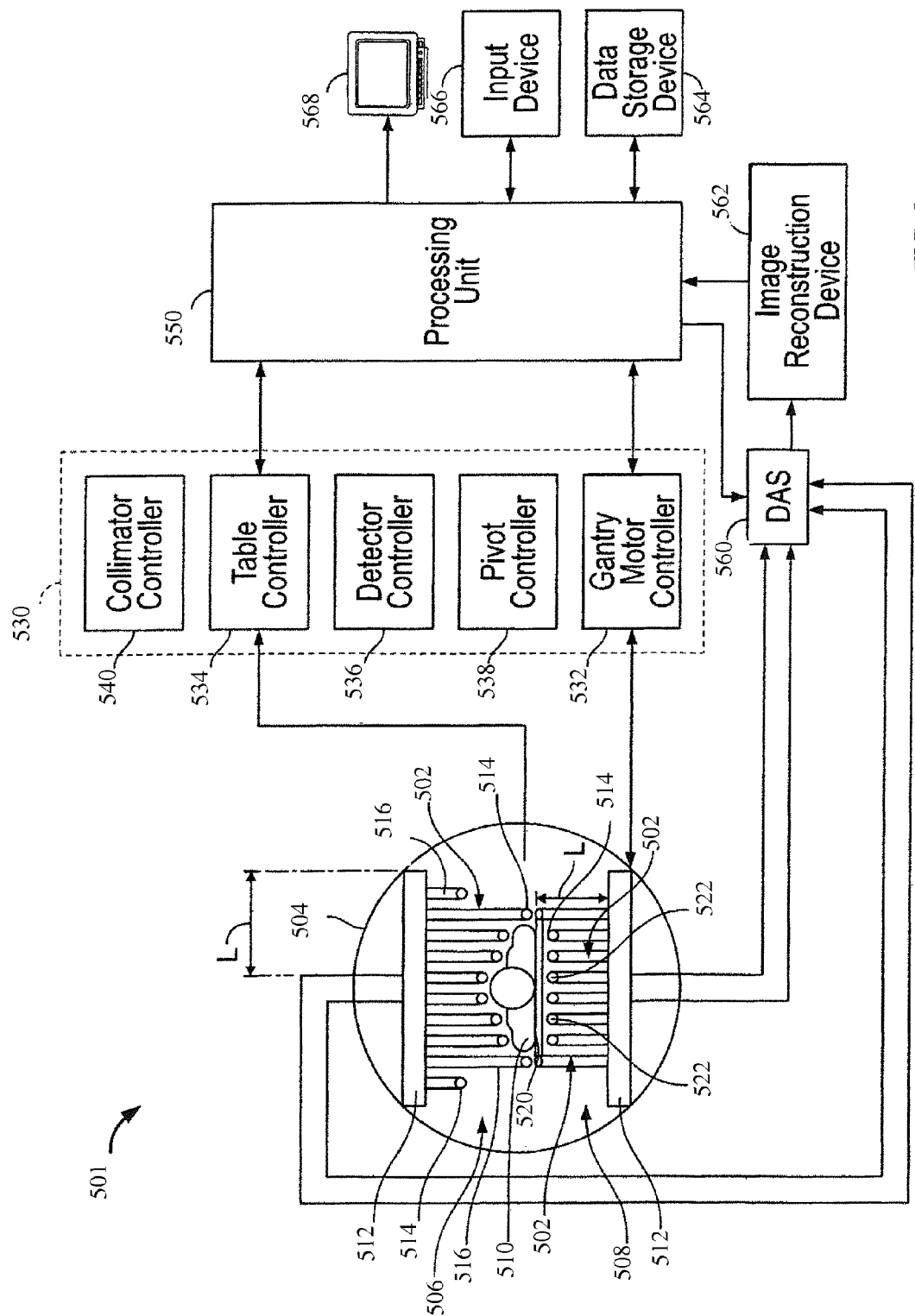
FIG. 9 is a schematic block diagram illustrating a NM imaging system in accordance with another embodiment.
Figure 10:
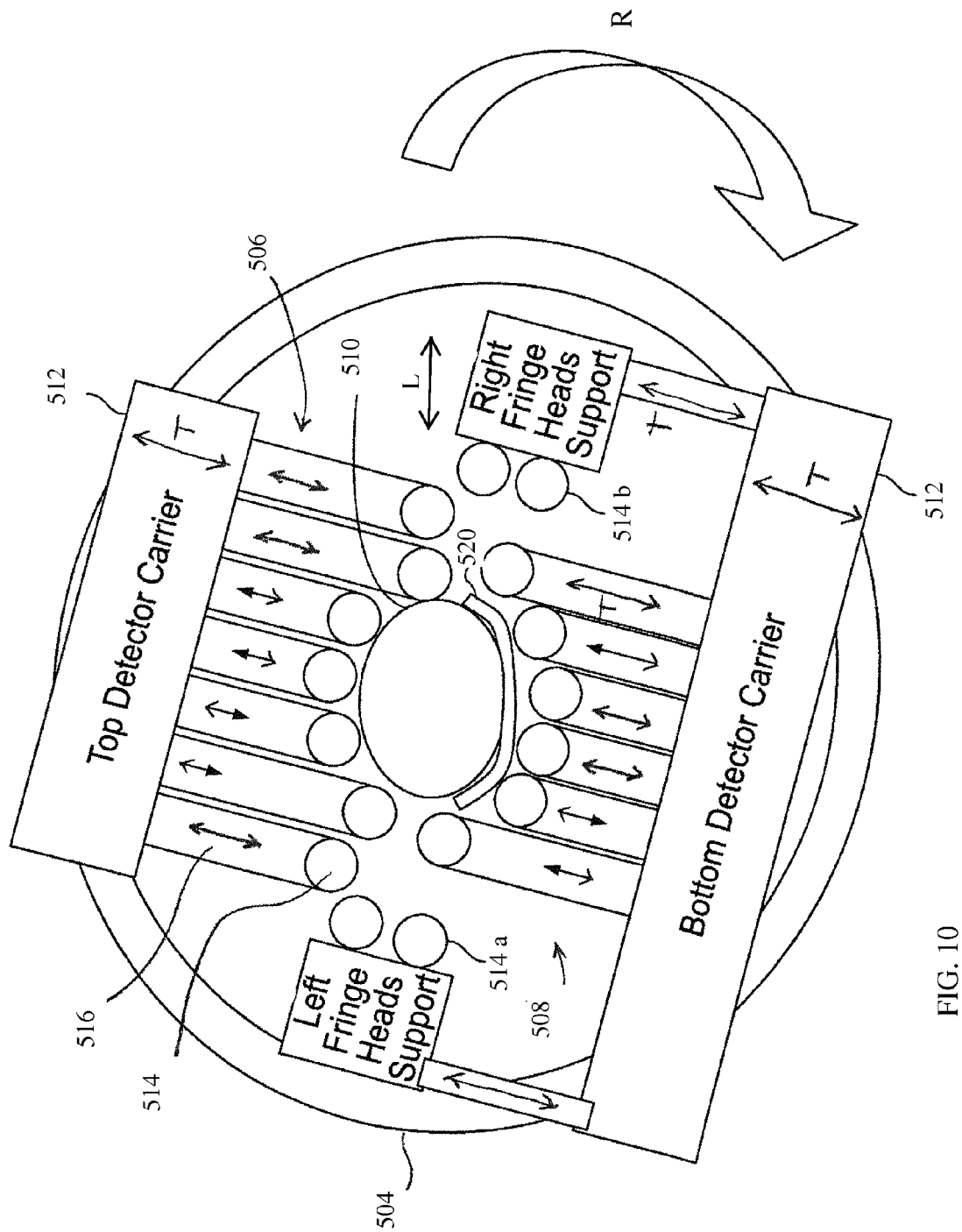
FIG. 10 is a schematic block diagram illustrating movable detector carriers of the NM imaging system shown in FIG. 9.

It should be noted that the movements of different detector units 314 likewise may be performed simultaneously, concurrently, or sequentially. It should be noted that while the movement is illustrated radially in FIGS. 5-7, translation movement in other transverse or perpendicular directions may be provided, such as left and right or up and down (as shown in FIGS. 9-10). Further, the various movements of the detector units 314 may be provided using any suitable drive and control means, such as using one or more motors. Additionally or optionally, a proximity sensor (not shown) or other patient safety device may be used to detect contact or impending contact with a patient. The proximity sensor may be provided in some embodiments as known in the art.

A controller unit 330 may control the movement and positioning of the patient table 310, imaging detectors 302 (which may include one or more arms 316), the gantry 304, and/or the collimators 322 (that move with the imaging detectors 302 in various embodiments, being coupled thereto). A range of motion before or during an acquisition, or between different image acquisitions, is set to maintain the actual FOV of each of the imaging detectors 302 directed, for example, towards or "aimed at" a particular area or ROI (of multiple ROIs) of the subject 310 or along the entire subject 310. The motion may be a combined or complex motion in multiple directions simultaneously, concurrently, or sequentially as described in more detail herein.

The controller unit 330 may have a gantry motor controller 332, table controller 334, detector controller 336, pivot controller 338, and collimator controller 340. The controllers 330, 332, 334, 336, 338, 340 may be automatically commanded by a processing unit 350, manually controlled by an operator, or a combination thereof. The gantry motor controller 332 may move the imaging detectors 302 with respect to the subject 310, for example, individually, in segments or subsets, or simultaneously in a fixed relationship to one another. For example, in some embodiments, the gantry controller 332 may cause the imaging detectors 302 and/or arms 316 to move relative to or rotate about the subject 310, which may include motion of less than or up to 180 degrees (or more).

The table controller 334 may move the patient table 320 to position the subject 310 relative to the imaging detectors 302. The patient table 320 may be moved in up-down directions, in-out directions, and right-left directions, for example. The detector controller 336 may control movement of each of the imaging detectors 302 to move together as a group or individually as described in more detail herein. The detector controller 336 also may control movement of the imaging detectors 302 in some embodiments to move closer to and farther from a surface of the subject 310, such as by controlling radial movement of the arms 316 towards or away from the subject 310 (e.g., sliding or telescoping movement).

The pivot controller 338 may control pivoting or rotating movement of the detector units 314 at ends of the arms 316 and/or rotating movement of the arms 316. For example, one or more of the detector units 314 or arms 316 may be rotated about at least one axis to view the subject 310 from a plurality of angular orientations to acquire, for example, 3D image data in a 3D SPECT or 3D imaging mode of operation. The collimator controller 340 may adjust a position of an adjustable collimator, such as a collimator with adjustable strips or adjustable pinhole(s).

It should be noted that motion of one or more imaging detectors 302 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 336 and pivot controller 338 may be combined to provide the different movements described herein.

Prior to acquiring an image of the subject 310 or a portion of the subject 310, the imaging detectors 310, gantry 304, patient table 320 and/or collimators 322 may be adjusted as discussed in more detail herein, such as to first or initial imaging positions, as well as subsequent imaging positions. The imaging detectors 302 may each be positioned to image a portion of the subject 310. Alternatively, one or more of the imaging detectors 302 may not be used to acquire data in a retracted position away from the subject 310. Positioning may be accomplished manually by the operator and/or automatically, which may include using, for example, image information such as other images acquired before the current acquisition, such as by the CT imaging system 401 or another imaging modality such as an MRI, X-Ray, PET or ultrasound. Additionally, the detector units 314 may be configured to acquire non-NM data, such as x-ray CT data.

After the imaging detectors 302, gantry 304, patient table 320, and/or collimators 322 are positioned, one or more images, such as three-dimensional (3D) SPECT images are acquired using one or more of the imaging detectors 302, which may include using a combined motion that reduces or minimizes spacing between detector units 314. The image data acquired by each imaging detector 302 may be combined and reconstructed into a composite image or 3D images in various embodiments.

In one embodiment, at least one of the arms 316, gantry 304, patient table 320, and/or collimators 322 are moved after being initially positioned, which includes individual movement of one or more of the detector units 314 (e.g., combined lateral and pivoting movement). For example, at least one of the arms 316 may be moved radially while pivoted. Thus, in various embodiments, a plurality of small sized detectors, such as the detector units 314 may be used for 3D imaging, such as when moving or sweeping the detector units 314 in combination with other movements.

In various embodiments, a data acquisition system (DAS) 360 receives electrical signal data produced by the imaging detectors 302 and converts this data into digital signals for subsequent processing. However, in various embodiments, digital signals are generated by the imaging detectors 302. An image reconstruction device 362 (which may be a processing device or computer) and a data storage device 364 may be provided in addition to the processing unit 350. It should be noted that one or more functions related to one or more of data acquisition, motion control, data processing and image reconstruction may be accomplished through hardware, software and/or by shared processing resources, which may be located within or near the imaging system 300, or may be located remotely. Additionally, a user input device 366 may be provided to receive user inputs (e.g., control commands), as well as a display 368 for displaying images.

Optionally, a detector position controller may be implemented in hardware, software, or a combination thereof, such as the detector position controller described and shown in a co-pending U.S. patent application Ser. No. 14/016,939, entitled "METHODS AND SYSTEMS FOR CONTROLLING MOVEMENT OF DETECTORS HAVING MULTIPLE DETECTOR HEADS," which is hereby incorporated by reference in its entirety. The detector position controller may form part of or operate in connection with the processing unit 350. In some embodiments, the detector position controller may be a module that operates to control the movement of the imaging detectors 302, including the detector units 314, such that coordinated or synchronized movement is provided as described herein. It should be noted that movement of a plurality of the imaging detectors 302 and/or detector units 314 may be performed at the same time (e.g., simultaneously or concurrently) or at different times (e.g., sequentially or step wise, such as back and forth between two detector units 314).

FIG. 9 is a schematic illustration of another embodiment of the NM imaging system 501 of the dual-modality imaging system 300. The imaging detectors 502 are configured as two separate detector arrays 506 and 508 coupled to a gantry 504 above and below a subject 510 (e.g., a patient). The detector arrays 506 and 508 may be coupled directly to the gantry 504, or may be coupled via support members 512 to the gantry 504 to allow movement of the entire arrays 506 and/or 508 relative to the gantry 504 (e.g., translating movement in the left or right direction as viewed in FIG. 4). Additionally, each of the imaging detectors 502 include a detector unit 514, at least some of which are mounted to a movable detector carrier 516 (e.g., a support arm or actuator that may be driven by a motor to cause movement thereof) that extends from the gantry 504. In some embodiments, the detector carriers 516 allow movement of the detector units 514 towards and away from the subject 510, such as linearly. Thus, in the illustrated embodiment the detector arrays 506 and 508 are mounted in parallel above and below the subject 510 and allow linear movement of the detector units 514 in one direction (indicated by the arrow L), illustrated as perpendicular to the support member 512 (that are coupled generally horizontally on the gantry 504). However, other configurations and orientations are possible as described herein. It should be noted that the movable detector carrier 516 may be any type of support that allows movement of the detector units 514 relative to the support member 512 and/or gantry 504, which in various embodiments allows the detector units 514 to move linearly towards and away from the support member 512.

A controller unit 530 may control the movement and positioning of the patient table 510, imaging detectors 502 (which may be configured as one or more arms), gantry 504 and/or the collimators 522 (that move with the imaging detectors 502 in various embodiments, being coupled thereto). A range of motion before or during an acquisition, or between different image acquisitions, is set to maintain the actual FOV of each of the imaging detectors 502 directed, for example, towards or "aimed at" a particular area or ROI of the subject 510 or along the entire subject 510. The motion may be a combined or complex motion in multiple directions simultaneously, concurrently, or sequentially as described in more detail herein.

The controller unit 530 may have a gantry motor controller 532, table controller 534, detector controller 536, pivot controller 538, and collimator controller 540. The controllers 530, 532, 534, 536, 538, 540 may be automatically commanded by a processing unit 550, manually controlled by an operator, or a combination thereof. The gantry motor controller 532 may move the imaging detectors 502 with respect to the subject 510, for example, individually, in segments or subsets, or simultaneously in a fixed relationship to one another. For example, in some embodiments, the gantry controller 532 may cause the imaging detectors 502 and/or support members 512 to move relative to or rotate about the subject 510, which may include motion of less than or up to 180 degrees (or more).

The table controller 534 may move the patient table 520 to position the subject 510 relative to the imaging detectors 502. The patient table 520 may be moved in up-down directions, in-out directions, and right-left directions, for example. The detector controller 536 may control movement of each of the imaging detectors 502 to move together as a group or individually as described in more detail herein. The detector controller 536 also may control movement of the imaging detectors 502 in some embodiments to move closer to and farther from a surface of the subject 510, such as by controlling translating movement of the detector carriers 516 linearly towards or away from the subject 510 (e.g., sliding or telescoping movement). Optionally, the detector controller 536 may control movement of the detector carriers 516 to allow movement of the detector array 506 or 508. For example, the detector controller 336 may control lateral movement of the detector carriers 516 illustrated by the L arrow (and shown as left and right as viewed in FIG. 7). In various embodiments, the detector controller 536 may control the detector carriers 516 or the support members 512 to move in different lateral directions.

The pivot controller 538 may control pivoting or rotating movement of the detector units 514 at ends of the detector carriers 516 and/or pivoting or rotating movement of the detector carrier 516. For example, one or more of the detector units 514 or detector carriers 516 may be rotated about at least one axis to view the subject 510 from a plurality of angular orientations to acquire, for example, 3D image data in a 3D SPECT or 3D imaging mode of operation. The collimator controller 540 may adjust a position of an adjustable collimator, such as a collimator with adjustable strips or adjustable pinhole(s).

It should be noted that motion of one or more imaging detectors 502 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 536 and pivot controller 538 may be combined to provide the different movements described herein.

Prior to acquiring an image of the subject 510 or a portion of the subject 510, the imaging detectors 510, gantry 504, patient table 520 and/or collimators 522 may be adjusted as discussed in more detail herein, such as to first or initial imaging positions, as well as subsequent imaging positions. The imaging detectors 502 may each be positioned to image a portion of the subject 510. Alternatively, one or more of the imaging detectors 502 may not be used to acquire data, such as the imaging detectors 502 at ends of the detector arrays 506 and 508, in a retracted position away from the subject 510. Positioning may be accomplished manually by the operator and/or automatically, which may include using, for example, image information such as other images acquired before the current acquisition, such as by the CT imaging system 401 or another imaging modality such as an MRI, X-Ray, PET or ultrasound. Additionally, the detector units 514 may be configured to acquire non-NM data, such as x-ray CT data.

After the imaging detectors 502, gantry 504, patient table 520, and/or collimators 522 are positioned, one or more images, such as three-dimensional (3D) SPECT images are acquired using one or more of the imaging detectors 502, which may include using a combined motion that reduces or minimizes spacing between detector units 514. The image data acquired by each imaging detector 502 may be combined and reconstructed into a composite image or 3D images in various embodiments.

In one embodiment, at least one of detector arrays 506 and/or 508, gantry 504, patient table 520, and/or collimators 522 are moved after being initially positioned, which includes individual movement of one or more of the detector units 514 (e.g., combined lateral and pivoting movement). For example, at least one of detector arrays 506 and/or 508 may be moved laterally while pivoted. Thus, in various embodiments, a plurality of small sized detectors, such as the detector units 514 may be used for 3D imaging, such as when moving or sweeping the detector units 514 in combination with other movements.

In various embodiments, a data acquisition system (DAS) 560 receives electrical signal data produced by the imaging detectors 502 and converts this data into digital signals for subsequent processing. However, in various embodiments, digital signals are generated by the imaging detectors 502. An image reconstruction device 562 (which may be a processing device or computer) and a data storage device 564 may be provided in addition to the processing unit 550. It should be noted that one or more functions related to one or more of data acquisition, motion control, data processing and image reconstruction may be accomplished through hardware, software and/or by shared processing resources, which may be located within or near the imaging system 300, or may be located remotely. Additionally, a user input device 566 may be provided to receive user inputs (e.g., control commands), as well as a display 568 for displaying images.

In operation, and as shown, for example, in FIG. 10, one embodiment includes two detector arrays 506 and 508 (in opposed parallel alignment) that allow movement of a plurality of detector units 514, illustrated as detector heads at the distal ends of a plurality of the detector carriers 516. In this embodiment, the two detector arrays 506 and 508 are top and bottom detector arrays, respectively, wherein the subject 510 is positioned therebetween on the patient table 520 with the detector array 506 above the subject 510 and the detector array 508 below the subject 510. As can be seen, the detector units 514 of the detector arrays 506 or 508 are generally supported along a plane of the support member 512 and moveable relative thereto. For example, the support members 512 may be generally planar with each of the detector units 514 moveable with respect to the support member 512 such that the detector units 514 move along parallel axes relative to the plane of the support member 512 (e.g., perpendicular to the plane of the support member 512 while maintaining a parallel relationship). Alternatively, in some embodiments, the lower support member 512 is configured to move in unison with the up/down bed motion (e.g., moved simultaneously or concurrently with the patient bed 520), but may not be coupled to the patient bed 520. It should be noted that the detector arrays 506 and 508 are contained within the footprint of the gantry as described herein.

In the illustrated embodiment, each of the detector units 514 of the detector array 506 is individually and independently controllable to translate the detector units 514 upwards and downwards with respect to the subject 510. For example, one or more of the detector units 514 in the detector array 506 is operable to translate down until the detector unit 514 is proximate or adjacent to the body of the subject 510, while not contacting or colliding with the subject 510. The distance of the detector units 514 from the subject 510 may be controlled using one or more proximity sensors as known in the art. Thus, as shown in FIG. 10, a plurality of the detector units 514 of the detector array 506 are moved towards and positioned proximate or adjacent the subject 510 (wherein some of the detector units 512 are positioned at different distances from the support member 512 than other detector units 512).

It should be noted that optionally the support member 512 may be moved to facilitate positioning of the detector units 514. For example, depending on the size of the subject 510 and the maximum length of the detector carriers 516, the support member 512 of the detector array 506 may likewise move towards or away from the subject 510 (as illustrated by the T arrows), such that all of the detector units 514 are moved together to a position closer or farther from the subject 510 (e.g., coarse movement) with the individual detector units 514 thereafter moved to position each in proximity or adjacent to the subject 510 (e.g., fine tuning movement). The support members 512 also may provide other optional movement, such as later movement (left and right as viewed in FIG. 9) as illustrated by the L arrow. For example, depending on the size or shape of the subject 510 and the positioning of the patient table 520, the support member 512 may initially translate to align the detector array 506 in a direction parallel to the coronal plane of the subject 520.

The detector units 514 in the detector array 508 in the illustrated embodiment are in a fixed position relative to the patient bed 520. For example, the detector units 514 may be fixedly mounted to the gantry 504 or to the support member 512 below the subject 510. In some embodiments, the detector carriers 516 are provided and may be fixed such that translating movement is not provided. In other embodiments, the detector carriers 516 are not provided with the detector units 514 fixedly mounted directly or through another fastening means (e.g., bracket) to the gantry 504 or to the support member 512 below the subject 510. However, in other embodiments the detector units 514 below the subject 510 may be movable with respect to the patient table 310. In various embodiments, the detector units 514 below the subject 520 are still individually rotatable or tiltable, while in other embodiments no movement is provided. Thus, the detector units 514 below the subject 510 may be movable or non-movable.

It should be noted that the positioning of the plurality of detector units 514, in particular each of the individual detector units 514 in the detector array 506 and/or 508 may be provided at the same time (e.g., concurrently or simultaneously) or at different times (e.g., sequentially).

In operation, once positioned, the gantry 504 may rotate the imaging detectors 502 about the subject 510 as illustrated by the R arrow. Thus, as illustrated in FIG. 10, the detector units 514 may be positioned in different radial positions around the subject 510, which may include translating movement of the detector units 514 to avoid contact with the subject 510.

Optionally, one or more of the detector units 514 of the detector array 506 may rotate, for example, along the examination axis and/or transverse (e.g., perpendicular) to the examination axis to view the subject 510 from a plurality of different orientations. The movement of the detector units 514 may be, for example, stepwise or continuous through a range of motion. The detector units 514 of the detector array 508 likewise may rotate. The detector units 514 of the detector arrays 506 and 508 may rotate at the same time (e.g., concurrently or simultaneously) or may rotate at different times (e.g., sequentially).

It should be noted that variations and modifications are contemplated. For example, one or more edge detector units 514a and 514b optionally may be located outside the edge of the patient table 520 such that movement from below the patient table 520 to a position above the patient table 520 (e.g., adjacent a side of the subject 510) may be provided. The detector units 514a and 514b may be positioned orthogonally with respect to the detector carrier 516 to point sideways towards the subject 510. In one embodiment, the other detector units 514 of the detector array 508 are fixed, while in other embodiments one or more of the other detector units 514 may be configured for movement as described herein.

Thus, in operation, the parallel movement of the detector units 514 in the detector array 506 above the subject 510 and with respect to each other allows positioning of the detector units 514 relative to any size subject 510. For example, each of the detector units 514 may be individually translated downward to be positioned in proximity or adjacent to a portion of the patient 510. Additionally, because the detector units 514 within the detector array 506 or 508 move along the same parallel planes (e.g., upwards and downwards in respective linear directions), the detector units 514 may be positioned with respect to subjects 510 having different sizes and shapes, while maintaining the same lateral gap between each of the detector units 514. In various embodiments, an increased number of detector units 514 then may be used when imaging a larger subject 510. Further configurations of the detector units 514 are described and shown, for example, in a co-pending U.S. patent application Ser. No. 14/016,943, entitled "SYSTEMS AND METHODS FOR PLANAR IMAGING WITH DETECTORS HAVING MOVING DETECTOR HEADS," which is hereby incorporated by reference in its entirety.

FIG. 11 is a perspective view of a dual-modality system 600 having an integrated housing 602 that includes a nuclear medicine (NM) gantry 604 and a computer tomography (CT) gantry 606 that are each concentrically oriented about a gantry central bore 607, such as along an examination axis. Alternatively, rather than the integrated housing 602, two housings may be used having the NM gantry 604 or the CT gantry 606 respectively. The gantry 604 is configured to support one or more NM cameras 608, such as, gamma cameras or SPECT detectors. The gantry 606 is configured to support an x-ray source 610 and a substantially diametrically opposed x-ray detector 612 for (CT) scans. The x-ray detector 612 in some embodiments includes a plurality of detector elements that are arranged in rows and channels that together sense the projected x-rays that pass through an object, such as a patient. The gantries 604 and 606 are further configured to rotate co-axially about an examination axis 614 and may rotate at different rotational speeds relative to each other.

A patient table 616 includes a bed 618 slidingly coupled to a bed support system 620, which is coupled directly to a floor or coupled to the gantry 602 through a base 621 coupled to gantry 602. The bed 618 may include a stretcher 622 slidingly coupled to an upper surface 624 of the bed 618. The patient table 616 is configured to facilitate ingress and egress of a patient into an examination position that is substantially aligned with the examination axis 614.

During an imaging scan, the patient table 616 is controlled to move the bed 618 and/or stretcher 622 axially into the bore 607 to bring a patient or a region of interest (ROI) through a NM scan field of view (FOV) 631 and a CT scan FOV 632. Once in the NM scan FOV 631, the rotor 604 may rotate at a relatively low rotational speed, for example, three rotations per minute. After the NM scan, the patient table 616 moves the bed 618 and/or stretcher 622 to bring the patient into the CT scan FOV 632. Once in the CT scan FOV 632, the gantry 606 may rotate at a relatively higher rotational speed, for example, three rotations per second.

Figure 12:
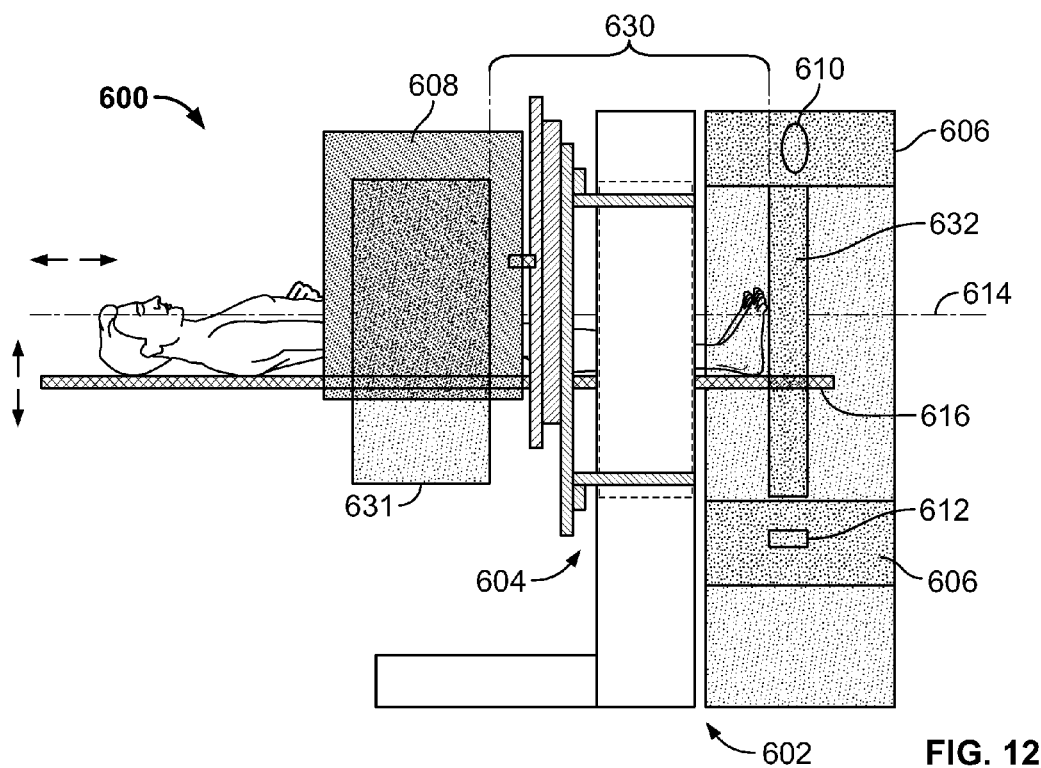
FIG. 12 is an illustration of a side view of a dual-modality system in accordance with another embodiment.

As illustrated in FIG. 12, the gantry 604 and the NM camera 608 create a FOV gap 630, approximately 1 meter long, between the two modalities. The FOV gap 630 may result in issues when acquiring images from the NM or CT scans. For example, as the patient table 616 travels through the bore 607, the patient table 616 may sag due to the weight of the patient. The sagging adversely affects the images acquired by the NM or CT scans and processing of the data merging or registering the images acquired images by creating image distortions, double imaging, and the like. The bed support system 620 may be configured using a telescopic motion (not shown) or motion extension in some embodiments to reduce the sagging of the patient table 616 while traveling through the bore 607, such as the apparatus described and shown in U.S. Pat. No. 8,126,537 entitle "METHOD AND APPARATUS FOR A MULTI-MODALITY IMAGING SYSTEM," which is hereby incorporated by reference in its entirety.

Further, the FOV gap 630 may create discomfort for the patient traveling through the bore 607. For example, the FOV gap 630 may extend the travel time between the two modalities by 60 seconds increasing the likelihood the patient may experience claustrophobia, move, or shift between scans or during the NM or CT scan, adversely affecting the images acquired by the NM or CT scans, such as creating image distortions, double imaging, and the like.

Figure 13:
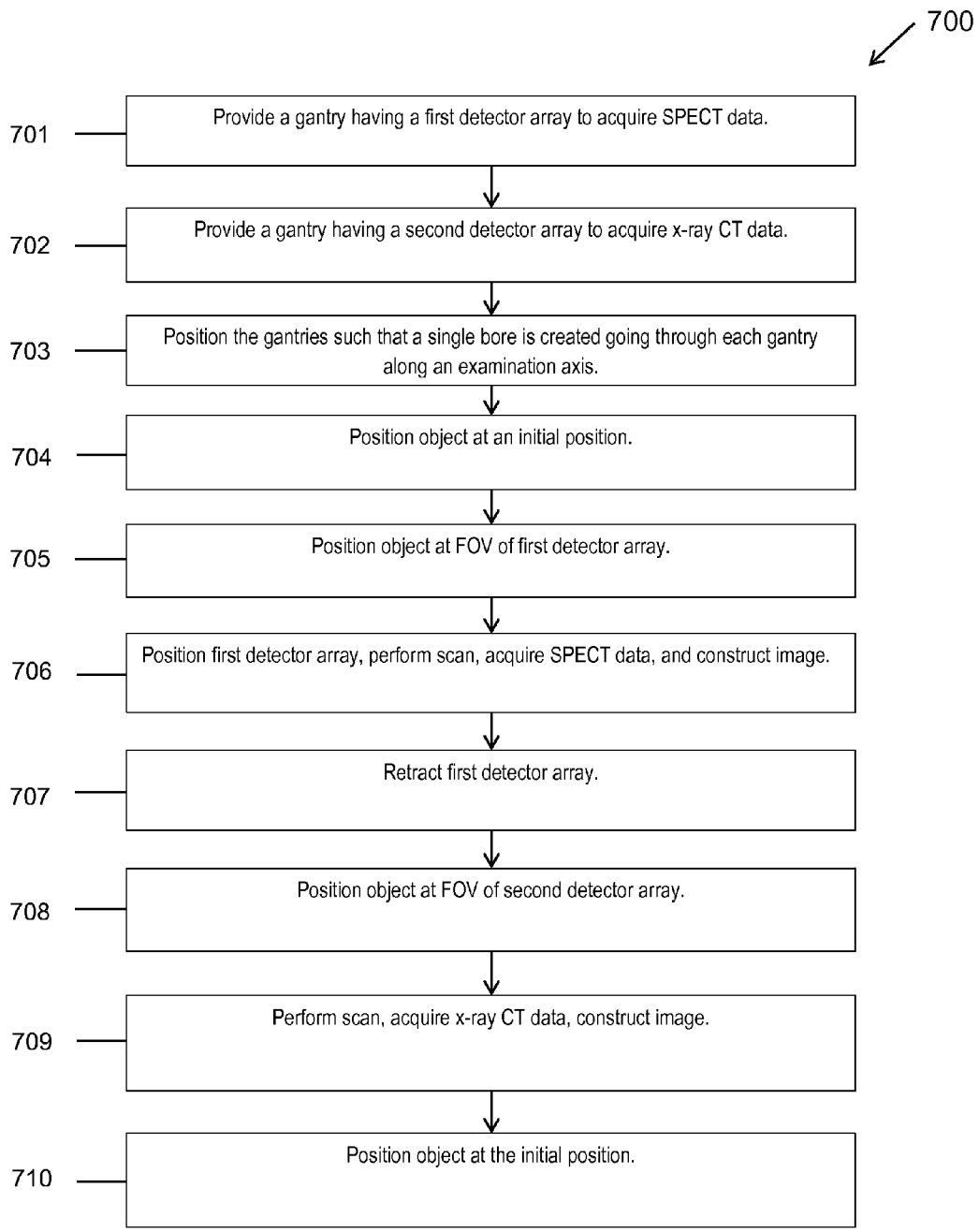
FIG. 13 is a flowchart of a method in accordance with various embodiments

Various embodiments also provide a method 700 as shown in FIG. 13. The method 700, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 700 may be able to be used as one or more algorithms to direct hardware to perform one or more operations described herein.

At 701, the method provides a gantry having a first detector array to acquire SPECT data, for example, the NM imaging systems 301 and 501 described herein wherein the detector units are contained within the footprints of the gantries (e.g., in particular, within the bores of the systems). At 702, the method provides a gantry having a second detector array to acquire x-ray CT data, for example, the CT imaging system 401 having an x-ray source 411 and an x-ray detector 410 as described herein. Further, at 703 the method positions the gantries such that a single bore is created going through each gantry along an examination axis. For example, the dual-modality imaging system 300 described herein having the single bore 318 along the examination axis 383. Alternatively, in an embodiment, the first detector array may acquire x-ray CT data and the second detector array acquiring SPECT data. For example, the x-ray CT data acquired by the first detector array may be used to isolate or narrow the region of interest of the object to be scanned by the second detector array acquiring SPECT data.

At 704, the method includes positioning an object at an initial (or loading) position. It should be noted that the positioning may be performed manually, semi-automatically, or automatically. The object, for example, may be the subjects 310 and/or 510 (e.g., human patients). At the initial position, the subject may be placed on a bed (e.g., the patent table 320) which is located outside a FOV of the first detector array or imaging modality. The bed may be advanced along the examination axis (e.g., 383) through the gantry (e.g., 304, 504). As the bed advances along the examination axis the bed traverses the FOV of the first and second detector arrays.

At 705, the method includes positioning the object at a FOV of the first detector array. Once the object is in position, at 706, the method positioning the first detector array to perform a scan, and acquire SPECT data, which is used to reconstruct an image. Thereafter, the method includes retracting the first detector array, at 707. For example, the method may include positioning the object at the NM FOV 382 of the NM imaging system 301 which acquires SPECT data. When the object is in position, the arms 316 may be moved radially inward or toward the object, positioning the detector units 314 adjacent to the object into the imaging position as described above. During the scan, the detector units 314 may acquiring SPECT data while rotating about the fixed pivot point 355 along the sweep range transverse to the subject 310 and/or examination axis (e.g., the examination axis 383). The image may be reconstructed using the SPECT data obtained during the scan, for example, by the image reconstruction device 362. It should be noted that imaging techniques such as binning or gating, among others, may be employed in various embodiments.

At 708, the method includes positioning the object at a FOV of the second detector array. Once the object is in position, at 709, the method includes performing a scan, acquiring x-ray CT data, and reconstructing an image. Thereafter, the method includes positioning the object at the initial position, at 710, such as removing the patient from the common bore in a reverse direction along the examination axis. For example, the method may include positioning the object at the CT FOV 482 of the CT imaging system 401 which acquires x-ray CT data. During the scan the x-ray detector 410 acquires x-ray CT data and then the patient is returned to the initial or loading position. The image may be reconstructed using the x-ray CT data obtain during the scan. It should be noted that the CT data acquisition and image reconstruction may be performed using different methods and techniques in the art.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §612, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A medical imaging system comprising:
   a first gantry having a plurality of first detector units coupled within a bore of the first gantry, wherein the first detector units form a first field of view (FOV) of the first gantry, the first detector units configured to acquire Single Photon Emission Computed Tomography (SPECT);
   a second gantry having a plurality of second detector units coupled within a bore of the second gantry, wherein the second detector units form a second FOV of the second gantry, the second detector units configured to acquire x-ray computed tomography (CT) data, the second gantry positioned adjacent to the first gantry;
   a common bore along an examination axis through the first and second gantries;
   a patient table movable through the common bore of the first and second gantry along the examination axis; and
   a controller unit configured to control a rotation speed of the first detector units and the second detector units around the examination axis.

2. The medical imaging system of claim 1, wherein the rotation speed of the first detector units are less than the rotation speed of the second detector units.

3. The medical imaging system of claim 1, wherein a collimator is coupled to at least one of the plurality of first detector units, the plurality of first detector units individually movable including translational movement towards or away from the patient table and when in an imaging position the plurality of first detector units are configured for rotational movement along a sweep range traverse to the patient table.

4. The medical imaging system of claim 1, wherein the plurality of first detector units are positioned to form an iris or linear configuration.

5. The medical imaging system of claim 1, wherein an edge of the first FOV and an edge of the second FOV are less than 50 cm apart.

6. The medical imaging system of claim 1, wherein an edge of the first FOV and an edge of the second FOV are less than 40 cm apart.

7. The medical imaging system of claim 1, wherein an edge of the first FOV and an edge of the second FOV are less than 30 cm apart.

8. The medical imaging system of claim 1, wherein the first gantry comprises a plurality of arms that move radially inward or outward relative to the common bore of the first gantry, wherein the first detector units are coupled to the plurality of arms.

9. The medical imaging system of claim 1, wherein the first gantry is positioned in front of the second gantry such that the patient table moves within the first FOV before entering the second FOV when moving along the examination axis.

10. The medical imaging system of claim 1, wherein the second gantry is positioned in front of the first gantry such that the patient table moves within the second FOV before entering the first FOV when moving along the examination axis.

11. The medical imaging system of claim 1, wherein the first and second gantries are formed from a common housing.

12. A medical imaging system comprising:
a gantry defining a housing and having a bore therethrough;
a patient table movable through the bore along an examination axis;
a plurality of detector units coupled within the bore, wherein a collimator is coupled to at least one of the plurality of detector units, the plurality of detector units individually movable including translational movement towards or away from the patient table and when in an imaging position the plurality of detector units are configured for rotational movement along a sweep range traverse to the patient table;
at least one x-ray source and at least one x-ray detector unit coupled within the bore, wherein the x-ray detector unit is configured to acquire x-ray data; and
a controller configured to control movement of the gantry and to control movement of the plurality of detector units including both the translational movement and the rotational movement to acquire Single Photon Emission Computed Tomography (SPECT) data from the plurality of detector units and x-ray computed tomography (CT) data from the x-ray detector unit.

13. The medical imaging system of claim 12, further comprising a plurality of arms configured to move radially inward or outward relative to the bore, wherein the plurality of detector units are coupled to the plurality of arms.

14. A method of obtaining a multimodality image of a patient, the method comprising:
providing a nuclear medicine-computer tomography (NM-CT) multimodality imaging system having a gap between a field of view (FOV) of NM detectors and a FOV of CT detector of less than 50 cm; and
acquiring a CT image and an NM image of a patient, wherein the acquiring of the CT image and the NM image of the patient is performed without repositioning the patient with respect to the patient table, and wherein the CT image and the NM image overlap over at least 120 cm along a length of the patient.

* * * * *